US009953248B2

(12) United States Patent
Cho

(10) Patent No.: US 9,953,248 B2
(45) Date of Patent: Apr. 24, 2018

(54) METHOD AND APPARATUS FOR IMAGE ANALYSIS

(71) Applicant: Samsung Electronics Co., Ltd., Gyeonggi-do (KR)

(72) Inventor: Seong Ho Cho, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 21 days.

(21) Appl. No.: 14/991,094

(22) Filed: Jan. 8, 2016

(65) Prior Publication Data

US 2016/0210536 A1 Jul. 21, 2016

(30) Foreign Application Priority Data

Jan. 15, 2015 (KR) ........................ 10-2015-0007236

(51) Int. Cl.
| G06K 9/00 | (2006.01) |
| G06K 9/78 | (2006.01) |
| G06F 19/00 | (2018.01) |
| G06K 9/22 | (2006.01) |
| G06K 9/46 | (2006.01) |
| A23L 33/00 | (2016.01) |

(52) U.S. Cl.
CPC ............... *G06K 9/78* (2013.01); *A23L 33/30* (2016.08); *G06F 19/321* (2013.01); *G06F 19/3475* (2013.01); *G06K 9/00208* (2013.01); *G06K 9/22* (2013.01); *G06K 9/4642* (2013.01); *G06K 9/4671* (2013.01); *A23V 2002/00* (2013.01); *G06K 2209/17* (2013.01)

(58) Field of Classification Search
CPC ...... G06K 9/78; G06K 9/4671; G06K 9/4642; G06K 9/22; G06K 2209/17; G06K 9/00208; A23L 33/30; A23V 2002/00; G06F 19/321; G06F 19/3475
USPC .......................................................... 382/128
See application file for complete search history.

(56) References Cited

U.S. PATENT DOCUMENTS

| 8,363,913 | B2 | 1/2013 | Boushey et al. |
| 8,392,957 | B2 | 3/2013 | Holt et al. |
| 8,548,459 | B1 * | 10/2013 | Carmody .............. H04W 24/04 |
| | | | 455/423 |
| 8,605,952 | B2 | 12/2013 | Boushey et al. |
| 9,177,225 | B1 * | 11/2015 | Cordova-Diba .......... G06T 5/00 |
| 2010/0111383 | A1 | 5/2010 | Boushey et al. |

(Continued)

FOREIGN PATENT DOCUMENTS

| KR | 10-2006-0122111 A | 11/2006 |
| KR | 10-2009-0046991 A | 5/2009 |
| WO | 2012/170587 A2 | 12/2012 |

OTHER PUBLICATIONS

European Search Report, dated Jun. 13, 2016.

*Primary Examiner* — Gregory F Cunningham
(74) *Attorney, Agent, or Firm* — Cha & Reiter, LLC

(57) ABSTRACT

An electronic device comprising: a memory; a communication circuit; and at least one processor operatively coupled to the memory and the communication circuit, configured to: obtain a first image; extract a feature associated with an object depicted in the first image; and control the communication circuit to transmit an indication of the feature to a server; and receive analysis information associated with the object from the server through the communication circuit.

20 Claims, 12 Drawing Sheets

(56) References Cited

U.S. PATENT DOCUMENTS

| | | |
|---|---|---|
| 2010/0277611 A1 | 11/2010 | Holt et al. |
| 2012/0179665 A1* | 7/2012 | Baarman ............. G06F 19/3475 |
| | | 707/709 |
| 2013/0004923 A1 | 1/2013 | Utter, II |
| 2013/0113933 A1 | 5/2013 | Boushey et al. |
| 2015/0092979 A1* | 4/2015 | Meredith ........... G06K 9/00577 |
| | | 382/103 |

* cited by examiner

METHOD AND APPARATUS FOR IMAGE ANALYSIS

CLAIM OF PRIORITY

This application claims the benefit under 35 U.S.C. § 119(a) of a Korean patent application filed on Jan. 15, 2015 in the Korean Intellectual Property Office and assigned Serial number 10-2015-0007236, the entire disclosure of which is hereby incorporated by reference.

TECHNICAL FIELD

The present disclosure relates to electronic devices, in general, and more particularly to a method and apparatus for image analysis.

BACKGROUND

A camera may be generally mounted on a portable device such as a smartphone, a hand-held device, and a tablet personal computer (PC). In general, while carrying such the device, a user may take a picture of a desired object, store the picture in the device, and share the picture with other users.

However, information that a user is capable of obtaining from an image captured by a user terminal is limited. Alternatively, as the performance of a camera mounted on a terminal is improved, the size of an image becomes also larger. Accordingly, in order to obtain detailed analysis information, a method of requesting an analysis by transmitting an image to a server may cause a large amount of data traffic.

SUMMARY

According to aspects of the disclosure, an electronic device is provided comprising: a memory; a communication circuit; and at least one processor operatively coupled to the memory and the communication circuit, configured to: obtain a first image; extract a feature associated with an object depicted in the first image; and control the communication circuit to transmit an indication of the feature to a server; and receive analysis information associated with the object from the server through the communication circuit.

According to aspects of the disclosure, a server is provided comprising: A server comprising: a memory; a communication circuit; and at least one processor operatively coupled to the memory and the communication circuit, configured to: receive, from an electronic device, an indication of a feature of an object depicted in a first image, through the communication circuit; analyze the feature to obtain corresponding analysis information; and control the communication circuit to transmit the analysis information to the electronic device.

According to aspects of the disclosure, a method is provided comprising: obtaining, by an electronic device, an image; extracting, by the electronic device, a feature on an object depicted in the image; transmitting an indication of the feature to a server; and receiving analysis information associated with the object from the server.

DETAILED DESCRIPTION

Figure 1:
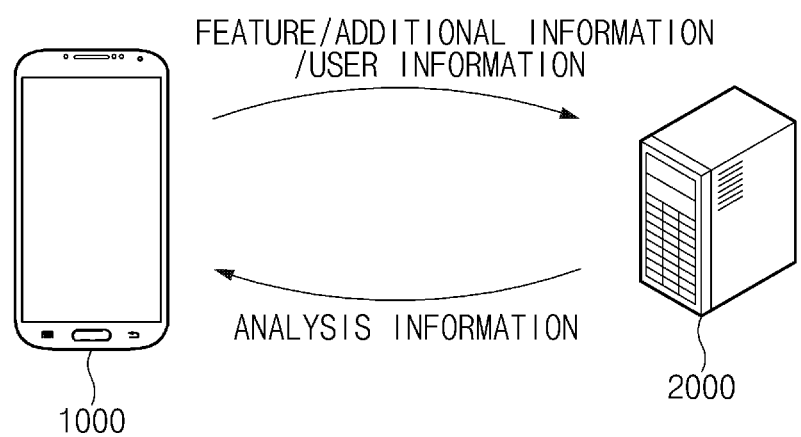
FIG. 1 is a diagram of an example of a system, according to an embodiment of the present disclosure.

Hereinafter, various embodiments of the present disclosure are disclosed with reference to the accompanying drawings. However, this does not limit various embodiments of the present disclosure to a specific embodiment, and it should be understood that the present disclosure covers all the modifications, equivalents, and/or alternatives of this disclosure provided they come within the scope of the appended claims and their equivalents. With respect to the descriptions of the drawings, like reference numerals refer to like elements.

The term "include," "comprise," and "have", or "may include," or "may comprise" and "may have" used herein indicates disclosed functions, operations, or existence of elements but does not exclude other functions, operations or elements.

For instance, the expression "A or B", or "at least one of A or/and B" may indicate include A, B, or both A and B. For instance, the expression "A or B", or "at least one of A or/and B" may indicate (1) at least one A, (2) at least one B, or (3) both at least one A and at least one B.

The terms such as "1st", "2nd", "first", "second", and the like used herein may refer to modifying various different elements of various embodiments of the present disclosure, but do not limit the elements. For instance, "a first user device" and "a second user device" may indicate different users regardless of the order or the importance. For example, a first component may be referred to as a second component and vice versa without departing from the scope of the present disclosure.

In various embodiments of the present disclosure, it will be understood that when a component (for example, a first component) is referred to as being "(operatively or communicatively) coupled with/to" or "connected to" another component (for example, a second component), the component may be directly connected to the other component or connected through another component (for example, a third component). In various embodiments of the present disclosure, it will be understood that when a component (for example, a first component) is referred to as being "directly connected to" or "directly access" another component (for example, a second component), another component (for example, a third component) does not exist between the component (for example, the first component) and the other component (for example, the second component).

The expression "configured to" used in various embodiments of the present disclosure may be interchangeably used with "suitable for", "having the capacity to", "designed to", "adapted to", "made to", or "capable of" according to a situation, for example. The term "configured to" may not necessarily mean "specifically designed to" in terms of hardware. Instead, the expression "a device configured to" in some situations may mean that the device and another device or part are "capable of." For example, "a processor configured to perform A, B, and C" in a phrase may mean a dedicated processor (for example, an embedded processor) for performing a corresponding operation or a generic-purpose processor (for example, a CPU or application processor) for performing corresponding operations by executing at least one software program stored in a memory device.

Terms used in various embodiments of the present disclosure are used to describe specific embodiments of the present disclosure, and are not intended to limit the scope of other embodiments. The terms of a singular form may include plural forms unless they have a clearly different meaning in the context. Otherwise indicated herein, all the terms used herein, which include technical or scientific terms, may have the same meaning that is generally understood by a person skilled in the art. In general, the terms defined in the dictionary should be considered to have the same meaning as the contextual meaning of the related art, and, unless clearly defined herein, should not be understood abnormally or as having an excessively formal meaning. In any cases, even the terms defined in this specification cannot be interpreted as excluding embodiments of the present disclosure.

Hereinafter, an electronic device according to various embodiments of the present disclosure will be described in more detail with reference to the accompanying drawings. The term "user" in this disclosure may refer to a person using an electronic device or a device using an electronic device (for example, an artificial intelligence (AI) electronic device).

FIG. 1 is a diagram of an example of a system, according to an embodiment of the present disclosure.

As illustrated, the system includes an electronic device 100 and a server 2000 in communication with each other through a wired or wireless network (e.g., the Internet, a Local Area Network, a Wide Area network, etc.).

The electronic device 1000 may correspond to one of a portable terminal such as a smartphone, a tablet PC, a notebook type PC, a portable digital assistant (PDA), and a personal media player (PMP), a fixed terminal such as a desktop PC, and a wearable device such as a smartwatch, a smart glasses and a head-mounted-device (HMD). In operation, the electronic device 1000 may obtain an image by capturing an image with a camera mounted thereon or receiving the image from another electronic device. The electronic device 1000 may then extract features associated with an object depicted in the obtained image and transmit the features to the server 2000. According to various embodiments of the present disclosure, in addition to the features extracted from the image, the electronic device 1000 may further transmit additional information associated with the image and/or user information associated with the electronic device 1000. A detailed configuration and operation of the electronic device 1000 will be described below with reference to FIGS. 2, 4, and 5.

The server 2000 may obtain analysis information related to the object depicted in the image by analyzing the features, the additional information, and/or the user information received from the electronic device 1000. The server 2000 may then transmit the analysis information (or analysis result) to the electronic device 1000. Afterwards, the electronic device 1000 may receive the analysis information and output at least some of it. A detailed configuration and operation of the server 2000 will be described with reference to FIGS. 3 and 9.

Figure 2:
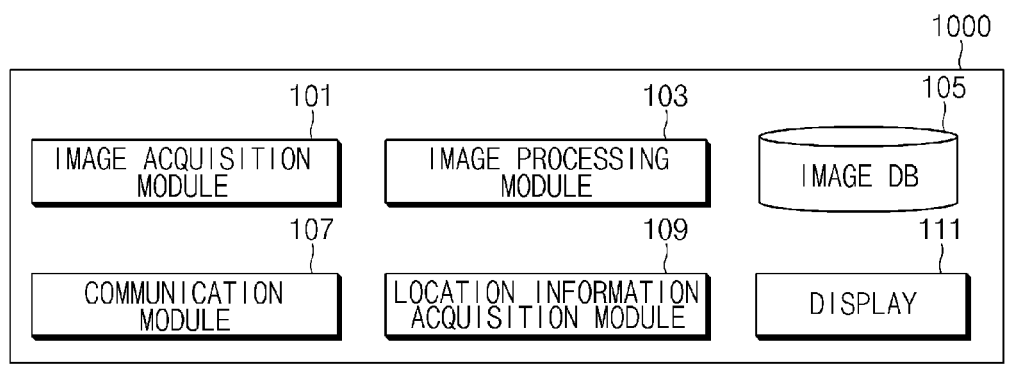
FIG. 2 is a diagram of an example of an electronic device, according to an embodiment of the present disclosure.

FIG. 2 is a diagram of an example of an electronic device, according to an embodiment of the present disclosure.

Referring to FIG. 2, an electronic device 1000 according to an embodiment of the present disclosure may include an image acquisition module 101, an image processing module 103, an image database (DB) 105, a communication module (or communication circuit) 107, a location information acquisition module 109, and a display 111. Although not shown in the drawing, a configuration of the electronic device 1000 is not limited to the listed configuration or the name of each component.

According to aspects of the disclosure, any of the image acquisition module 101, the image processing module 103, and the image DB 105 may be implemented in hardware, and/or as a combination of software and hardware. For example, any of the image acquisition module 101, the image processing module 103, and the image DB 105 may be implemented by using one or more processors. Each of the processors may include any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), etc.

In operation, the image acquisition module 101 may obtain an image. For example, the image acquisition module 101 may obtain an image captured by a camera module or receive a pre-generated image from an internal storage device or an external storage device. According to an embodiment of the present disclosure, the image may include a still image (for example, a key frame) that is extracted by the image acquisition module 101 from a specific video file.

The image processing module 103 may extract features of an object depicted in an image obtained by the image acquisition module 101. According to aspects of the disclosure, the term "object" may refer to any suitable type of physical object that is depicted in the image. For example, when a user take an image (photo) of a steak dish on a table, the steak dish itself becomes a subject of the image and the steak dish depicted on the image (for example, the image may include a steak dish, a table, and a background view) becomes an object.

As used throughout the disclosure, the term "feature" may refer to any suitable type of number, string, and/or alphanumerical string that is generated based on an image. For example, the term "feature" may refer to at least one of an image descriptor, MPEG standards Compact Descriptors for Visual Search (CDVS), Histograms of Oriented Gradient (HOG) feature, Scale Invariant Feature Transform (SIFT) feature, dense-SIFT feature, and Speeded Up Robust Features (SURF) feature.

According to an embodiment of the present disclosure, the image processing module 103 may identify the respective types of images obtained by the image acquisition module 101 based on at least one standard image stored in the image DB 105. For example, the image processing module 103 may generate a score indicating a degree of similarity between an obtained image and the standard image for a particular type of images (e.g., category) and determine that the obtained image is of the same type as the standard image based on the score. In other words, the image processing module 103 may classify the obtained image into a particular category by comparing the obtained image with one or more standard images that are retrieved from the image DB 105. The image processing module 103 may extract features from the classified image.

For example, the electronic device 1000 may extract features from an image depicting one or more food items and receive analysis information from the server 2000. In this case, the image processing module 103 of the electronic device 1000 may generate a plurality of respective scores representing a degree of similarity between an image (e.g., an image of a steak dish) obtained by the image acquisition module 101 and each of a plurality of standard images of different types (e.g., foods, landscapes, etc.) that are retrieved from the image DB 105. Afterwards, the image processing module 103 may identify the highest score in the plurality and determine that the obtained image is the same type as the standard image associated with the highest score.

In some implementations, when a plurality of images is obtained and stored in the memory of the electronic device, the image processing module 103 may extract features only from images that have been classified into a particular category (e.g., images that have been classified as "food" images). In this manner, when the images are classified according to type in advance, the electronic device 1000 may extract features from only an image classified as "food" without extracting features from all images stored in the electronic device 1000. By doing so, the electronic device 1000 may prevent the use of a resource unnecessary for image feature extraction.

Additionally or alternatively, according to an embodiment of the present disclosure, before extracting features, the image processing module 103 may select a portion of the obtained image that includes a particular object of interest. For example, when a user shoots an image of a steak dish on a table, it is possible to crop a portion of the image containing the depiction of the steak dish and calculate a feature corresponding to the steak dish based on the cropped portion. As a result of the cropping, other objects depicted in the image such as a glass cup, a fork, and a knife on the table may be excluded from a feature extraction target. Thus, an image area that is a feature extraction target may be reduced drastically.

Additionally or alternatively, the image processing module 103 may apply specified image processing (for example, Y-image conversion) to an image before extracting the feature. The image processing may support efficient feature extraction in addition to the cropping.

Additionally or alternatively, according to an embodiment of the present disclosure, the image processing module 103 may obtain additional information associated with the obtained image. By way of example, the additional information may include at least one of metadata of the image, an indication of a time when the image is obtained, and an indication of a location where the image is obtained.

The metadata, for example, may include the type, sensitivity, exposure information, shooting date and time, ISO value, focal length, or resolution of a shooting camera. For example, when the image acquisition module 101 obtains the image through a camera, the indication of the time when the image is obtained and/or the indication of the location where the image is obtained may correspond to a shooting date and time or a shooting place included in the metadata. However, when the image is received from another external device, the indication of the time when the image is obtained and/or the indication of the location where the image is obtained may be different from a shooting date and time or a shooting location included in the metadata.

In general, when image processing such as Y-image conversion or cropping is performed, metadata added to an image may be deleted or changed. Accordingly, the image processing module 103 may obtain metadata in advance before performing image processing or store the metadata in an additional storage space or the image DB 105.

The image DB 105 may store at least one standard image. For example, the standard image may correspond to an image (or the feature of an image) having a known type. For example, when the type is "food", a standard image for "food" may include an image of rice, kimchi stew, steak, or bread and in the case that the type is "travel", a standard image for "travel" may include an image of Gyeongbokgung, Seokguram, the Eiffel Tower, or the Statue of Liberty. The image processing module 103 may classify images obtained by the image acquisition module 101 according to a predetermined type by referring to standard images included in the image DB 105.

The communication module (or communication circuit) 107 may transmit features extracted from the image and/or additional information to the server 2000. Additionally, or alternatively, the communication module 107 may further transmit user information associated with the electronic device 1000. By way of example, user information may include information associated with a particular account (e.g., a Samsung account) of a user using the electronic device 1000.

According to an embodiment of the present disclosure, the communication module 107 may receive analysis information from the server 2000. By way of example, the analysis information may be analysis information of an object relating to features extracted from the image. For example, when features extracted from an image relate to a steak dish depicted in the image and are transmitted to the server 2000, the server 2000 may transmit, to the electronic device 1000, at least one of an indication of one or more ingredients of the dish depicted in the image, nutritional information associated with the dish depicted in the image, material information, a recipe for preparing the dish, and medical information associated with the dish and/or some of its ingredients.

The communication module 107 may connect the electronic device 1000 to the server 2000. The communication module 107, for example, may include at least one of a 3G/4G communication interface module, a WiFi module, a Bluetooth module, and a radio frequency (RF) module.

According to an embodiment of the present disclosure, the transmission/reception operation of the communication module 107 may be performed based on billing information of a network. For example, when connecting to a no cost network (for example, WiFi) or a relatively cheap network, the communication module 107 may perform an operation for transmitting the extracted features and receiving analysis information.

The location information acquisition module 109, for example, may obtain geographical location information of the electronic device 100 as including a Global Positioning System (GPS) module. According to various embodiments of the present disclosure, the location information acquisition module 109 may obtain or supplement location information based on currently accessed base station (for example, eNB) information or currently accessed access point (AP) information.

The display 111 may visually display analysis information received from the server 2000. The electronic device 1000 may display the analysis information on the display 111 by executing a specified application (for example, S-health application, 3rd party application, and so on).

Figure 3:
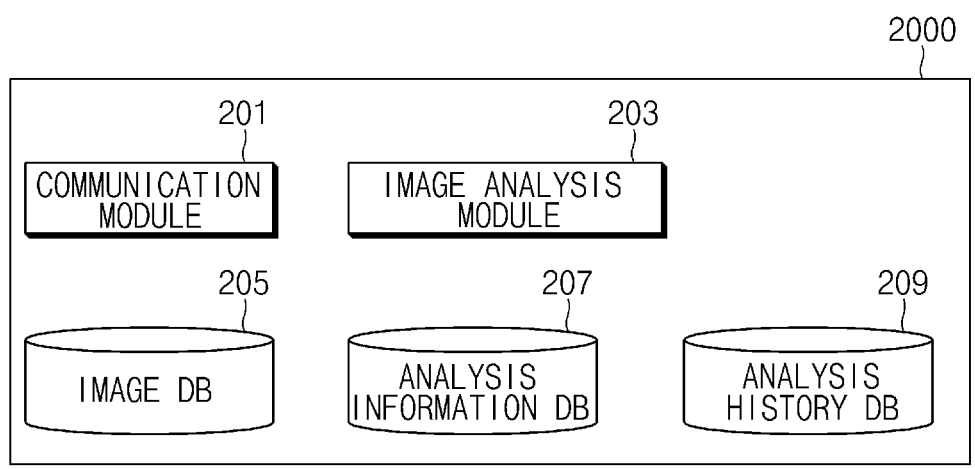
FIG. 3 is a diagram of an example of a server, according to an embodiment of the present disclosure.

FIG. 3 is a diagram of an example of a server, according to an embodiment of the present disclosure.

Referring to FIG. 3, a server 2000 may include a communication module (or communication circuit) 201, an image analysis module 203, an image DB 205, an analysis information DB 207, and an analysis history DB 209. According to aspects of the disclosure, any of the image analysis module 203, the image DB 205, the analysis information DB 207, and the analysis history DB 209 may be implemented in hardware, and/or as a combination of software and hardware. For example, the image analysis module 203, may be implemented by using one or more processors. Any of the image DB 205, the analysis information DB 207, and the analysis history DB 209 may be implemented in one or more internal/external memories. Each of the processors may include any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), etc.

The communication module (or communication circuit) 201 may receive features extracted from an image (hereinafter referred to as a first image) by the electronic device 1000, additional information associated with the first image, and/or user information of the electronic device 1000. According to an embodiment of the present disclosure, the communication module 201 may transmit analysis information obtained by the image analysis module 203 to the electronic device 1000.

Like the communication module 107 of the electronic device 1000, the communication module 201 may be used to connect the electronic device 1000 to the server 2000. The communication module 201, for example, may include at least one of 3G, LTE, and WiFi modules, a Bluetooth module, and an RF module.

In operation, the image analysis module 203 may analyze features received from the electronic device 1000 to obtain corresponding analysis information. For example, the image analysis module 203 may identify another image (hereinafter referred to as a second image (for example, a reference image)) that matches the first image. Afterwards, the image analysis module 203 may obtain analysis information based on the second image. According to aspects of the disclosure, the second image may be an image of known type that depicts the same (or similar) object as the first image (e.g., a steak dish). To detect that the first image and the second image match, the image analysis module 203 may use a local/global descriptor, a convolutional neural network (CNN) based classifier, and/or a Support Vector Machine (SVM) classifier.

According to various embodiments of the present disclosure, the second image may be retrieved from the image DB 205 included in a server and the analysis information may be retrieved from the analysis information DB 207. However, a method of determining the second image and obtaining analysis information is not limited to the above. The second image may be received from another server that includes a more extensive image DB and also the analysis information may be obtained from another server having more detailed analysis information.

For example, when features received from the electronic device 1000 are features associated with the depiction of a steak dish in the image, the image analysis module 203 may analyze the features and identify a second image that also depicts a steak dish. The second image may be retrieved from the image DB 205 (or an external server). The image analysis module 203 may obtain analysis information (for example, ingredient information, nutritional information, material information, recipes, or medical information) linked to the second image may be retrieved from the analysis information DB 207 (or an external server).

According to various embodiments of the present disclosure, the server 2000 may receive additional information from the electronic device 1000 in addition to the features. In such instances, the image analysis module 203 may obtain corresponding analysis information based on the features and/or the additional information. The additional information may include at least one of metadata of the first image, an indication of a time when the first image is obtained, and an indication of a location information where the first image is obtained.

For example, features extracted from the first image may include features associated with the steak dish that is depicted in the first image. Additionally or alternatively, for example, the additional information may include time information indicating that the first image was captured at night. In this case, in determining the second image by analyzing the features of steak, the image analysis module 203 may consider the time information. That is, when identifying the second image by referring to the image DB 205 (or an external server), the image analysis module 203 may exclude in advance an image of food normally eaten for breakfast. Thus, reliability in determining the second image may be further improved.

As another example, the features extracted from the first image may include the features associated with the depiction of the steak dish in the first image, and the additional information may include location information of a steak restaurant. In this case, in determining the second image, the image analysis module 203 may consider the location information of the steak restaurant That is, when determining the second image by referring to the image DB 205 (or an external server), the image analysis module 203 may first consider an image of food (for example, various steaks and mashed potatoes) that a typical steak restaurant provides. Thus, the reliability of identifying the second image may be further improved.

According to various embodiments of the present disclosure, various information included in the metadata of the first image may be analyzed together with the feature(s) extracted from the first image and may be used for searching for the second image.

According to various embodiments of the present disclosure, the server 2000 may receive user information associated with the electronic device 1000 in addition to any features that have been extracted from the first image. In such instances, the image analysis module 203 may obtain corresponding analysis information based on the features and/or the user information. The user information, as information for identifying the user of the electronic device 1000 from another user, may include information associated with an integrated service account (for example, Samsung account) for providing various embodiments of the present disclosure.

As an example, the feature(s) extracted from the first image may include a depiction of a steak dish, and the user information may include an user account for identifying user A. In this case, when identifying the second image by analyzing the feature(s) of the depiction of the steak dish, the image analysis module 203 may refer to the analysis history DB 209 for the user A. That is, when determining the second image by referring to the analysis history DB 209, the image analysis module 209 may first consider an image of food that the user A has eaten in the past. Additionally or alternatively, when obtaining analysis information, the image analysis module 203 may consider first analysis information associated with food that the user A has eaten in the past by referring to the analysis history DB 209.

The reliability of identifying the second image including a steak through the above-mentioned method may be further improved. Since the food intake habits of users tend to follow a regular pattern in general, the reliability of the first image or the analysis information may be further improved by referring to a user specific analysis history. Additionally or alternatively, in order to improve the reliability of an analysis result, an image of food that a user actually has eaten in the past and/or analysis information corresponding to this image may be stored in the analysis history DB 209 for future use.

The image DB 205 may store a plurality of images to be referred by the image analysis module 203. In some implementations, each of the plurality of images stored in the image DB 205 may be matched to an analysis information record that is stored in the analysis information DB 207, respectively. The image analysis module 203 may identify the second image including an object corresponding to features received from the electronic device 1000 by performing a search of the image DB 205.

According to various embodiments of the present disclosure, when the image analysis module 203 retrieves the second image by referring to an additionally prepared outside server, the image DB 205 may be omitted from the configuration of the server 2000.

The analysis information DB 207 may store a plurality of analysis information records which may be retrieved by the image analysis module 203. For example, the plurality of analysis information records corresponding to a plurality of images stored in the image DB 205 may be stored in the analysis information DB 207. The image analysis module 203 may obtain analysis information corresponding to the second image by referring to the analysis information DB 207.

According to various embodiments of the present disclosure, when the image analysis module 203 obtains the analysis information records by referring to an additionally prepared outside server, the analysis information DB 207 may be omitted from the analysis information DB 207.

The analysis history DB 209 may store records including analysis information obtained in the past by the image analysis module 203, for a plurality of different users. For example, each record stored in the analysis history DB 209 may have the format of: [user information]-[second image determined in the past]-[analysis information corresponding to second image determined in the past]. Additionally or alternatively, in some implementations, the record fields [second image determined in the past] or [analysis information corresponding to second image determined in the past] may be configured in a format specified by the image DB 205 or the analysis information DB 207, which respectively store them.

According to various embodiments of the present disclosure, since the electronic device 1000 transmits features extracted from an obtained image without transmitting an obtained image itself to the server 2000, data used for transmission may be drastically and relatively reduced. Furthermore, the reliability of the identification of analysis information by the server 2000 may be improved by transmitting additional information and/or user information to a server. By doing so, a user of the electronic device 1000 may receive useful and highly reliable analysis information.

Hereinafter, an image analyzing method according to various embodiments of the present disclosure will be described with reference to FIGS. 4 to 9.

Figure 4:
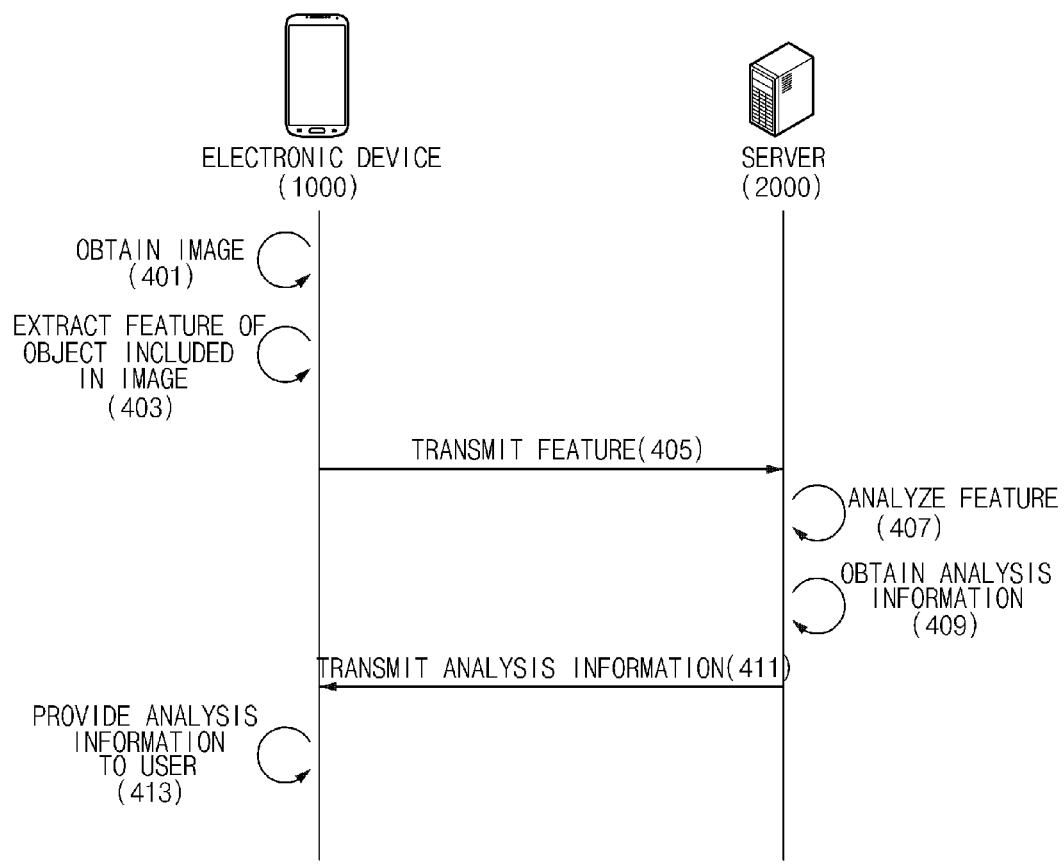
FIG. 4 is a sequence diagram of an example of a process, according to an embodiment of the present disclosure.

FIG. 4 is a sequence diagram of an example of a process, according to an embodiment of the present disclosure.

Referring to FIG. 4, the image acquisition module 101 of the electronic device 1000 may obtain an image including an object in operation 401. For example, the image acquisition module 101 may obtain an image captured by a camera or obtain a previously generated image from an internal storage device or an external storage device. Additionally or alternatively, the image acquisition module 101 may obtain the image by extracting one or more frames from a specific video file.

In operation 403, the image processing module 103 of the electronic device 1000 may extract one or more features associated with an object depicted in the image obtained in operation 401. The features of the object may include at least one of an image descriptor, MPEG standard CDVS, HOG feature, SIFT feature, dense-SIFT feature, and SURF feature.

In operation 405, the communication module 107 of the electronic device 1000 may transmit an indication of the feature(s) of the object to the server 2000. Additionally or alternatively, the communication module 201 of the server 2000 may receive the features of the object.

In operation 407, the image analysis module 203 of the server 2000 may analyze the received feature(s).

In operation 409, the image analysis module 203 of the server 2000 may obtain analysis information corresponding to the object based on the analysis performed in operation 407. By way of example, the image analysis module 203 may refer to at least one of the image DB 205, the analysis information DB 207, and the analysis history DB 209.

In operation 411, the communication module 201 of the server 2000 may transmit the obtained analysis information to the electronic device 1000. Additionally or alternatively, the communication module 107 of the electronic device 1000 may receive the analysis information associated with the object.

In operation 413, the display 111 of the electronic device 1000, for example, may output the received analysis information by using an application that is executed on the electronic device 1000.

Figure 5:
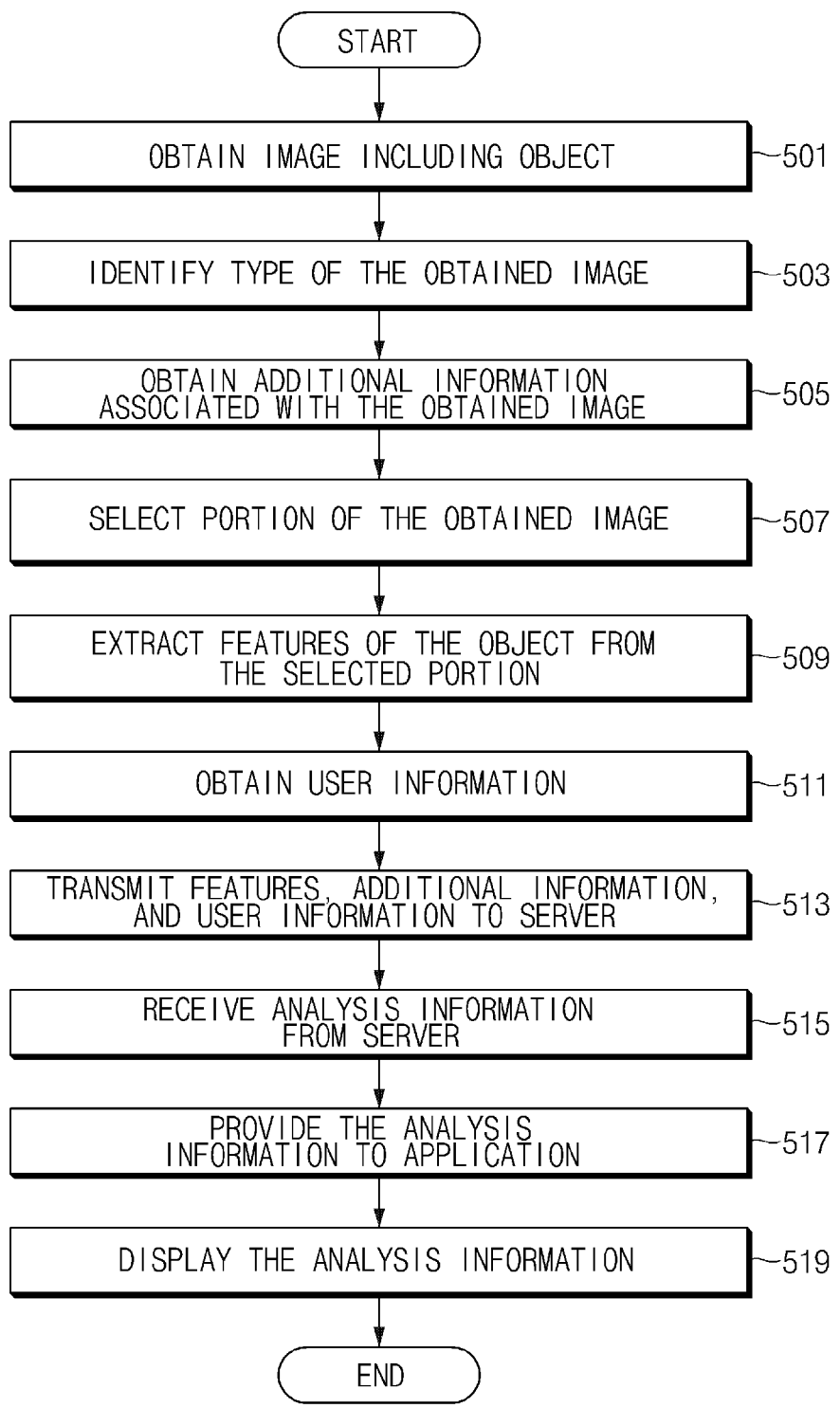
FIG. 5 is a flowchart of an example of a process, according to an embodiment of the present disclosure.

FIG. 5 is a flowchart of an example of a process for obtaining analysis information associated with a particular image, according to an embodiment of the present disclosure. FIGS. 6 to 8 are diagrams of a user interface for obtaining and presenting the analysis information, according to an embodiment of the present disclosure.

Figures 6A, 6B:
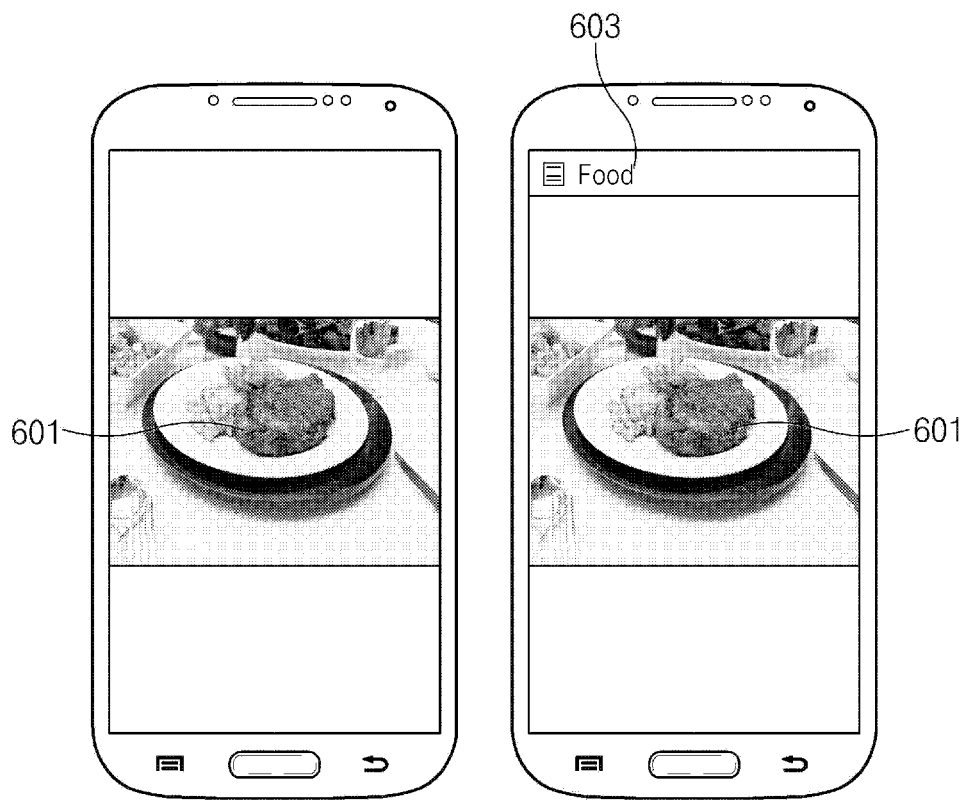
FIG. 6A is a diagram of an example of an image, according to an embodiment of the present disclosure.
FIG. 6B is a diagram of an example of an image after the image has been classified into a category, according to an embodiment of the present disclosure.

Referring to FIG. 5, the image acquisition module 101 of the electronic device 1000 may obtain an image including an object in operation 501. For example, the image acquisition module 101 may obtain an image including an object (e.g., a steak dish) as shown in FIG. 6A.

In operation 503, the image processing module 103 of the electronic device 1000 may identify the type of images obtained by the image acquisition module 101 based on at least one standard image that is stored in the image DB 105. For example, as shown in FIG. 6B, the image including the object (e.g., a steak dish) 601 may be classified as "food" image. In other words, the image shown in FIG. 6B may be classified into a "food" category 603 in response to detecting that the image matches a standard image that is associated with the "food" category. According to aspects of the disclosure, the image including the object may be considered to match the standard image when a score indicating the similarity between the two images exceeds a threshold and/or when the score is the highest from a plurality of scores that correspond to different standard images.

In operation 505, the image processing module 103 of the electronic device 1000 may obtain additional information associated with the image obtained in operation 501. The additional information may include at least one of metadata of the image, an indication of a time when the image is obtained, and an indication of a location where the image is obtained.

In operation 507, the image processing module 103 of the electronic device 1000 may select a specific portion of the image depicting a particular object. For example, the image processing module 103 may crop a portion of the image that includes an object that has been classified into the "food" category (or another predetermined category). By way of example, an image processing (for example, Y-image conversion) may be additionally applied.

Figures 6C, 6D:
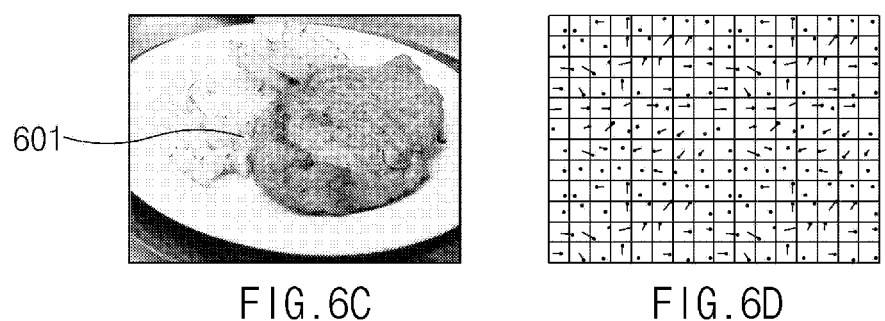
FIG. 6C is a diagram of an example of a portion of an image that includes an object of interest, according to an embodiment of the present disclosure.
FIG. 6D is a diagram of an example of an image feature, according to an embodiment of the present disclosure.

For example, as shown in FIG. 6C, the image processing module 103 may leave a specified area including the object (steak) 601 on the image of FIG. 6B and remove the depictions of the fork, and the glass from the image. Additionally or alternatively, the image of FIG. 6C may correspond to an image obtained when predetermined image processing (for, example, Y-image conversion processing) is applied to the image of FIG. 6A or 6B.

In operation 509, the image processing module 103 of the electronic device 1000 may calculate features of the object depicted in the selected portion of the image. In this regard, FIG. 6D illustrates an example of HOG features that are calculated based on the object (e.g., a steak dish) 601 that is selected from the image shown in FIG. 6C.

In operation 511, the image processing module 103 of the electronic device 1000 may obtain user information associated with the electronic device 1000. For example, information related to a service account of a user A of the electronic device 1000 may be obtained.

In operation 513, the communication module 107 of the electronic device 1000 may transmit, to the server 2000, an indication of the feature(s) extracted in operation 509, the additional information obtained in operation 505, and/or the user information obtained in operation 511.

In operation 515, the communication module 107 of the electronic device 1000 may receive from the server 2000 analysis information associated with the object. For example, the analysis information may include the ingredient information, nutritional information, material information, recipes, or medical information of the object (steak) 601 shown in FIGS. 6A to 6C.

In operation 517, the received analysis information may be provided to an application that is being executed, such as a food tracker or healthcare application.

FIGS. 7A to 7F illustrate an example of a food tracker of a healthcare application (S-health) that can receive the analysis information.

Figure 7A:
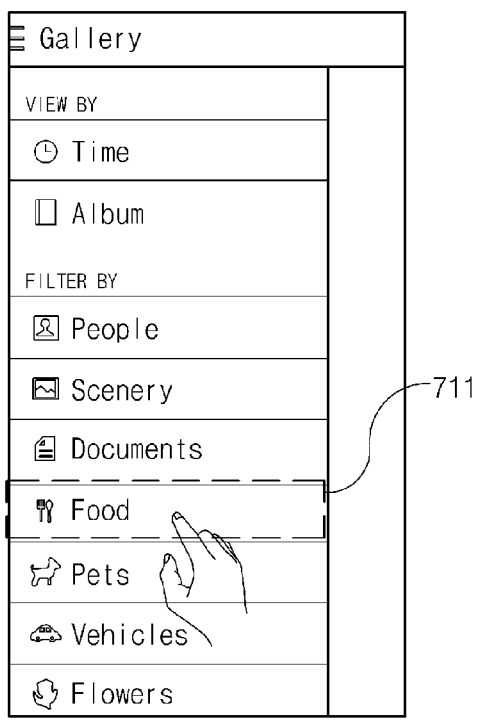
FIG. 7A is a diagram of an example of a user interface, according to an embodiment of the present disclosure.
Figure 7B:
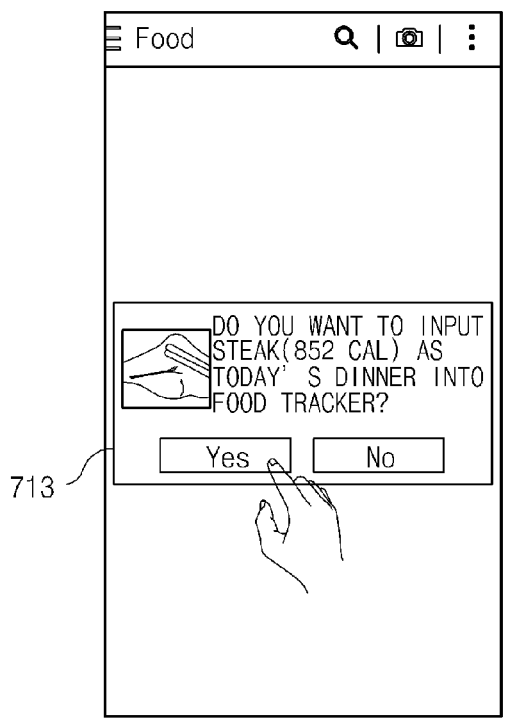
FIG. 7B is a diagram of an example of a user interface, according to an embodiment of the present disclosure.
Figure 7C:
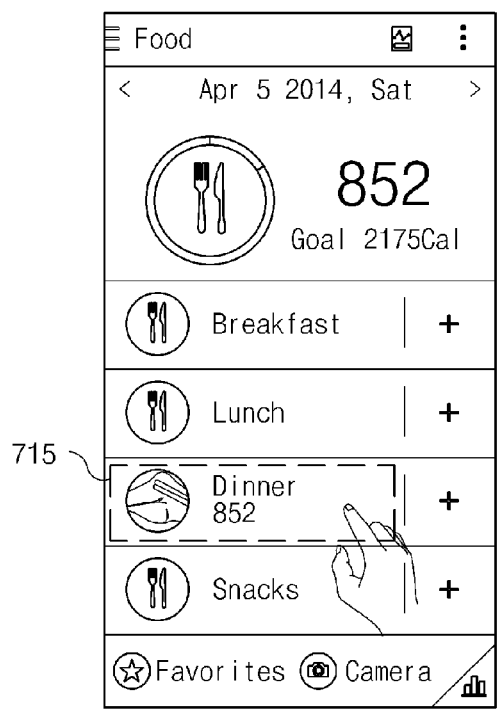
FIG. 7C is a diagram of an example of a user interface, according to an embodiment of the present disclosure.
Figure 8:
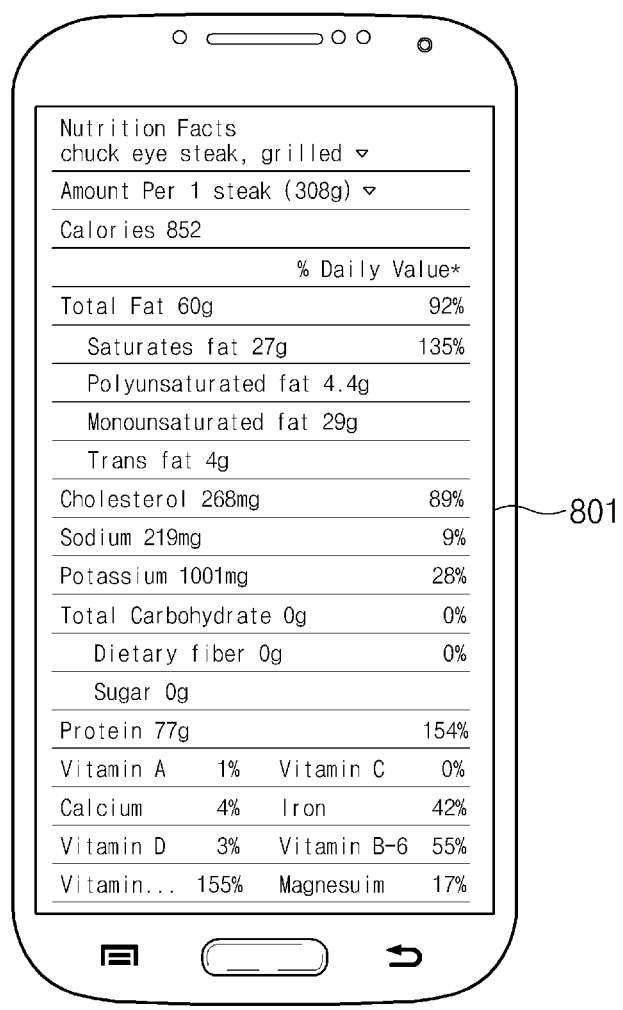
FIG. 8 is a diagram of an example of a user interface, according to an embodiment of the present disclosure.

Referring to FIGS. 7A to 7C, a user may execute a "Gallery" application that is a viewer application for displaying images and select a "Food" item 711 from a predetermined image classification (see FIG. 7A). When the "Food" item 711 is selected, a healthcare application executed on the background may provide, to a user, a notification 713 that analysis information related to the steak dish depicted in the image is received (see FIG. 7B). If the user presses the button "Yes," that is provided in the notification 713, the healthcare application may notify a user that a steak of 852 kcal is consumed as a dinner by reflecting the analysis information as shown in FIG. 7C.

Figure 7D:
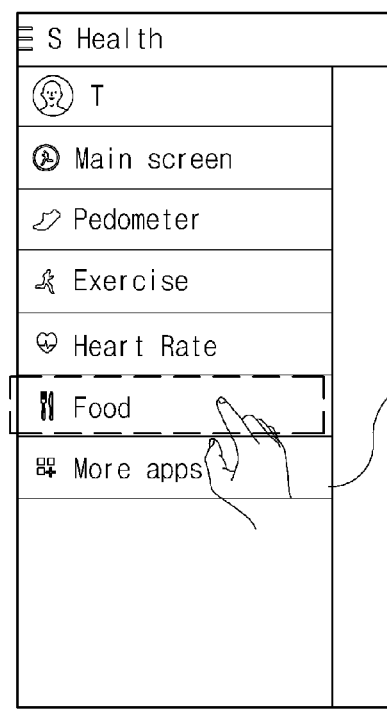
FIG. 7D is a diagram of an example of a user interface, according to an embodiment of the present disclosure.
Figure 7E:
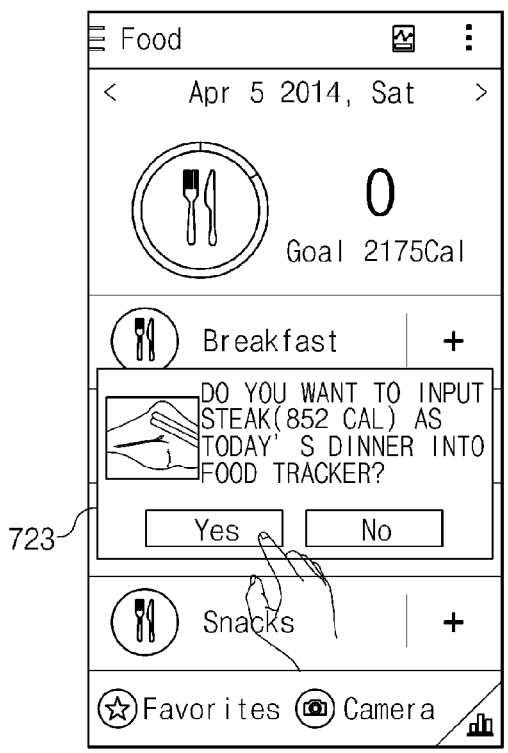
FIG. 7E is a diagram of an example of a user interface, according to an embodiment of the present disclosure.
Figure 7F:
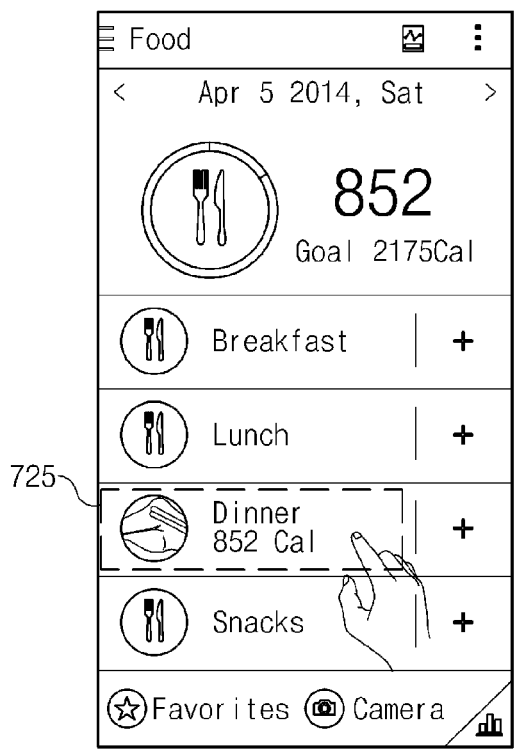
FIG. 7F is a diagram of an example of a user interface, according to an embodiment of the present disclosure.

Similarly, referring to FIGS. 7D to 7F, a user may select a "Food" item from various function lists by executing the healthcare application (see FIG. 7D). When the user selects the "Food" item by activating the input component 721 (e.g., a button), the healthcare application may provide, to a user, a notification 723 that analysis information associated with a steak dish is received (see FIG. 7E). If the user presses the button "Yes", the healthcare application may notify a user that a steak of 852 kcal is consumed as a dinner by reflecting the analysis information as shown in FIG. 7F.

In operation 519, the display 111 of the electronic device 1000 may display the analysis information to a user. For example, when the user selects one of the input components 715 and 725 (e.g., buttons), the screen 801 of FIG. 8 may be displayed on the display 111. The screen 801 provides the received analysis information corresponding to the food item associated with the selected input component. As illustrated, the screen 801 may include nutrition information for the steak dish (for example, calories 852 Kcal, fat 60 g, cholesterol 268 mg, sodium 219 mg, and so on). According to various embodiments of the present disclosure, a list of one or more ingredients of the steak dish, medical information associated with one or more ingredients of the steak dish, and the location of the restaurant where the steak dish was served may be further provided on the screen 801.

Figure 9:
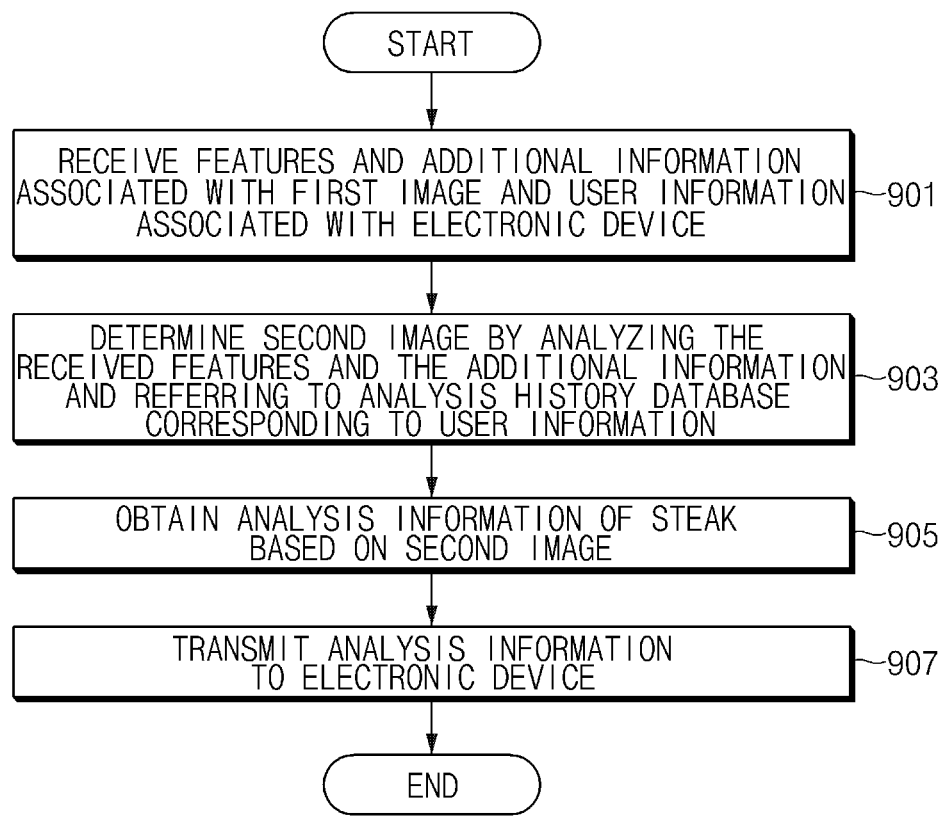
FIG. 9 is a flowchart of an example of a process, according to an embodiment of the present disclosure.

FIG. 9 is a flowchart of an example of a process, according to an embodiment of the present disclosure.

Referring to FIG. 9, for example, operation 901 to operation 907 of FIG. 9 may be performed between operation 513 and operation 515 of FIG. 5.

In operation 901, the communication module 201 of the server 2000 may receive features of an object included in a first image, additional information associated with the first image, and/or user information of the electronic device 1000.

In operation 903, the image analysis module 203 of the server 2000 may identify a second image based on the features and the additional information and referring to the image DB 205 and/or the analysis history DB 209 corresponding to the user information.

In operation 905, the image analysis module 203 of the server 2000 may obtain analysis information associated with a depiction of food in the second image by referring to the analysis information DB 207 and/or the analysis history DB 209 corresponding to the user information.

In operation 907, the communication module 201 of the server 2000 may transmit the analysis information obtained in operation 905 to the electronic device 1000.

Figure 10:
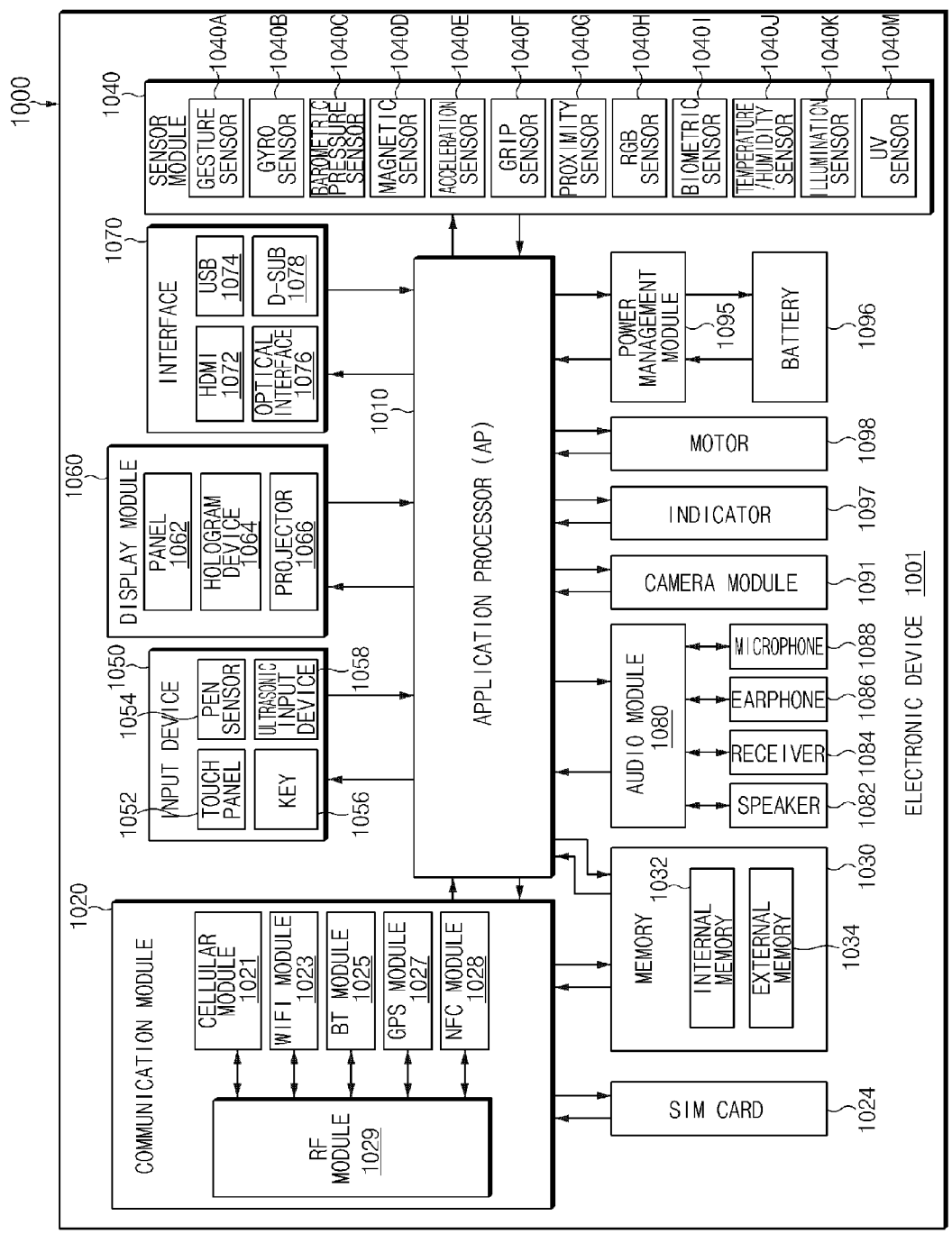
FIG. 10 is a diagram of an example of an electronic device, according to an embodiment of the present disclosure.

FIG. 10 is a block diagram of an electronic device 1001 according to various embodiments of the present disclosure.

Referring to FIG. 10, an electronic device 1001, for example, may configure all or part of the above-mentioned electronic device 1000 shown in FIG. 1. The electronic device 1001 may include at least one processor (for example, an application processor (AP) 1010), a communication module 1020, a subscriber identification module (SIM) 1024, a memory 1030, a sensor module 1040, an input device 1050, a display 1060, an interface 1070, an audio module 1080, a camera module 1091, a power management module 1095, a battery 1096, an indicator 1097, and a motor 1098.

The processor 1010 may include any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), etc. In operation, the processor 1010 may control a plurality of hardware or software components connected thereto and also may perform various data processing and operations by executing an operating system or an application program. The processor 1010 may be implemented with a system on chip (SoC), for example. According to an embodiment of the present disclosure, the processor 1010 may further include a graphic processing unit (GPU) and/or an image signal processor (for example, the image acquisition module 101 and the image processing module 103 of FIG. 2). The processor 1010 may load commands or data received from at least one of other components (for example, nonvolatile memory) and process them and may store various data in a nonvolatile memory.

The communication module 1020 (for example, the communication module 107) may include a cellular module 1021, a WiFi module 1023, a BT module 1025, a GPS module 1027 (for example, the location information acquisition module 109), an NFC module 1028, and a radio frequency (RF) module 1029.

The cellular module 1021, for example, may provide voice call, video call, text service, or internet service via a communication network. According to an embodiment of the present disclosure, the cellular module 1021 may perform a distinction and authentication operation on the electronic device 1001 in a communication network by using a SIM (for example, a SIM card) 1024. According to an embodiment of the present disclosure, the cellular module 1021 may perform at least part of a function that the processor 1010 provides. According to an embodiment of the present disclosure, the cellular module 1021 may further include a communication processor (CP).

Each of the WiFi module 1023, the BT module 1025, the GPS module 1027, and the NFC module 1028 may include a processor for processing data transmitted/received through a corresponding module. According to an embodiment of the present disclosure, at least part (for example, at least one) of the cellular module 1021, the WiFi module 1023, the BT module 1025, the GPS module 1027, and the NFC module 1028 may be included in one integrated chip (IC) or IC package.

The RF module 1029, for example, may transmit/receive communication signals (for example, RF signals). The RF module 1029, for example, may include a transceiver, a power amp module (PAM), a frequency filter, a low noise amplifier (LNA), or an antenna. According to another embodiment of the present disclosure, at least one of the cellular module 1021, the WiFi module 1023, the Bluetooth module 1025, the GPS module 1027, and the NFC module 1028 may transmit/receive RF signals through a separate RF module.

The SIM 1024, for example, may include a card including a SIM and/or an embedded SIM and also may include unique identification information (for example, an integrated circuit card identifier (ICCID)) or subscriber information (for example, an international mobile subscriber identity (IMSI)).

The memory 1030 may include any suitable type of volatile or non-volatile memory, such as Random-access Memory (RAM), Read-Only Memory (ROM), Network Accessible Storage (NAS), cloud storage, a Solid State Drive (SSD), etc. For example, the memory 1030 may include an internal memory 1032 or an external memory 1034. For example, the image DB 105 of FIG. 1 may be built in the memory 1030.

The internal memory 1032 may include at least one of a volatile memory (for example, dynamic RAM (DRAM), static RAM (SRAM), synchronous dynamic RAM (SDRAM)) and a non-volatile memory (for example, one-time programmable ROM (OTPROM), programmable ROM (PROM), erasable and programmable ROM (EPROM), electrically erasable and programmable ROM (EEPROM), mask ROM, flash ROM, flash memory (for example, NAND flash memory or NOR flash memory), hard drive, or solid state drive (SSD)).

The external memory 1034 may further include a flash drive, for example, compact flash (CF), secure digital (SD), micro Micro-SD, Mini-SD, extreme digital (xD), (MultiMediaCard (MMC), or a memory stick. The external memory 1034 may be functionally and/or physically connected to the electronic device 1000 through various interfaces.

The sensor module 1040 measures physical quantities or detects an operating state of the electronic device 1000, thereby converting the measured or detected information into electrical signals. The sensor module 1040 may include at least one of a gesture sensor 1040A, a gyro sensor 1040B, a barometric pressure sensor 1040C, a magnetic sensor 1040D, an acceleration sensor 1040E, a grip sensor 1040F, a proximity sensor 1040G, a color sensor 1040H (for example, a red, green, blue (RGB) sensor), a biometric sensor 1040I, a temperature/humidity sensor 1040J, an illumination sensor 1040K, and an ultraviolet (UV) sensor 1040M. Additionally or alternatively, the sensor module 1040 may include an E-nose sensor, an electromyography (EMG) sensor, an electroencephalogram (EEG) sensor, an electrocardiogram (ECG) sensor, an infrared (IR) sensor, an iris sensor, or a fingerprint sensor. The sensor module 1040 may further include a control circuit for controlling at least one sensor therein. According to an embodiment of the present disclosure, the electronic device 1000 may further include a processor configured to control the sensor module 1040 as part of or separately from the processor 1010 and thus may control the sensor module 1040 while the processor 1010 is in a sleep state.

The input device 1050 may include a touch panel 1052, a (digital) pen sensor 1054, a key 1056, or an ultrasonic input device 1058. The touch panel 1052 may use at least one of capacitive, resistive, infrared, or ultrasonic methods, for example. Additionally or alternatively, the touch panel 1052 may further include a control circuit. The touch panel 1052 may further include a tactile layer to provide tactile response to a user.

The (digital) pen sensor 1054, for example, may include a sheet for recognition as part of a touch panel or a separate sheet for recognition. The key 1056 may include a physical button, an optical key, or a keypad, for example. The ultrasonic input device 1058 may detect ultrasonic waves generated from an input tool through a microphone (for example, the microphone 1088) in order to check data corresponding to the detected ultrasonic waves.

The display 1060 (for example, the display 111 of FIG. 1) may include a panel 1062, a hologram device 1064, or a projector 1066. The panel 1062 may be implemented to be flexible, transparent, or wearable, for example. The panel 1062 and the touch panel 1052 may be configured with one module. The hologram 1064 may show three-dimensional images in the air by using the interference of light. The projector 1066 may display an image by projecting light on a screen. The screen, for example, may be placed inside or outside the electronic device 1000. According to an embodiment of the present disclosure, the display 1060 may further include a control circuit for controlling the panel 1062, the hologram device 1064, or the projector 1066.

The interface 1070 may include a high-definition multimedia interface (HDMI) 1072, a universal serial bus (USB) 1074, an optical interface 1076, or a D-subminiature (sub) 1078, for example. Additionally or alternatively, the interface 1070 may include a mobile high-definition link (MHL) interface, a secure Digital (SD) card/multimedia card (MMC) interface, or an infrared data association (IrDA) standard interface.

The audio module 1080 may convert sound into electrical signals and convert electrical signals into sounds. The audio module 1080 may process sound information inputted/outputted through a speaker 1082, a receiver 1084, an earphone 1086, or a microphone 1088.

The camera module 1091, as a device for capturing a still image and a video, may include at least one image sensor (for example, a front sensor or a rear sensor), a lens (not shown), an image signal processor (ISP) (not shown), or a flash (not shown) (for example, an LED or a xenon lamp).

The power management module 1095 may manage the power of the electronic device 1001. According to an embodiment of the present disclosure, the power management module 1095 may include a power management IC (PMIC), a charger IC, or a battery or fuel gauge, for example. The PMIC may have a wired and/or wireless charging method. As the wireless charging method, for example, there is a magnetic resonance method, a magnetic induction method, or an electromagnetic method. An additional circuit for wireless charging, for example, a circuit such as a coil loop, a resonant circuit, or a rectifier circuit, may be added. The battery gauge may measure the remaining amount of the battery 1096, or a voltage, current, or temperature thereof during charging. The battery 1096, for example, may include a rechargeable battery and/or a solar battery.

The indicator 1097 may display a specific state of the electronic device 1001 or part thereof (for example, the processor 1010), for example, a booting state, a message state, or a charging state. The motor 1098 may convert electrical signals into mechanical vibration and may generate vibration or haptic effect. Although not shown in the drawings, the electronic device 1000 may include a processing device (for example, a GPU) for mobile TV support. A processing device for mobile TV support may process media data according to the standards such as digital multimedia broadcasting (DMB), digital video broadcasting (DVB), or MediaFLO™.

According to various embodiments of the present disclosure, since an electronic device transmits features extracted from an obtained image instead of transmitting the obtained image itself to a server, data traffic of a network may be drastically reduced. Additionally or alternatively, useful and highly reliable analysis information corresponding to the features may be provided to a user.

Each of the above-mentioned components of the electronic device according to various embodiments of the present disclosure may be configured with at least one component and the name of a corresponding component may vary according to the kind of an electronic device. According to various embodiments of the present disclosure, an electronic device according to various embodiments of the present disclosure may include at least one of the above-mentioned components, may not include some of the above-mentioned components, or may further include another component. Additionally or alternatively, some of the components in an electronic device according to various embodiments of the present disclosure are configured as one entity, so that functions of previous corresponding components are performed identically.

FIGS. 1-10 are provided as an example only. At least some of the operations discussed with respect to these figures can be performed concurrently, performed in different order, and/or altogether omitted. It will be understood that the provision of the examples described herein, as well as clauses phrased as "such as," "e.g.", "including", "in some aspects," "in some implementations," and the like should not be interpreted as limiting the claimed subject matter to the specific examples. Although some of the above-discussed processes are performed in a client-server fashion by an electronic device 1000 and a server 2000, it will be understood that further implementations are possible in which some or all of the tasks performed by the server 2000 in the above-discussed processes are performed locally by the electronic device 1000.

The above-described aspects of the present disclosure can be implemented in hardware, firmware or via the execution of software or computer code that can be stored in a recording medium such as a CD-ROM, a Digital Versatile Disc (DVD), a magnetic tape, a RAM, a floppy disk, a hard disk, or a magneto-optical disk or computer code downloaded over a network originally stored on a remote recording medium or a non-transitory machine-readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for".

Moreover, the embodiments disclosed in this specification are suggested for the description and understanding of technical content but do not limit the range of the present disclosure. Accordingly, the range of the present disclosure should be interpreted as including all modifications or various other embodiments based on the technical idea of the present disclosure.

What is claimed is:

1. An electronic device, comprising:
    a memory;
    a communication circuit; and
    at least one processor operatively coupled to the memory and the communication circuit, configured to:
        obtain a first image and classifying the first image by executing a first comparison on the first image;
        in response to detecting that the first image is classified into a category of images stored in the memory, extract a feature associated with an object depicted in the first image; and
        control the communication circuit to transmit an indication of the feature to a server for execution of a second comparison by the server to retrieve analysis information corresponding to the feature; and
        receive the analysis information from the server through the communication circuit.

2. The electronic device of claim 1, wherein the category indicates the object is classified in a food item category, and the at least one processor is further configured to:
    in response to detecting a selection of the food item category from among a plurality of categories, display a selectable option to add the object to a list together with at least a portion of the analysis information received from the server.

3. The electronic device of claim 2, wherein the analysis information comprises at least one of:
    (i) an indication of one or more ingredients of the food item,
    (ii) nutritional information associated with the food item,
    (iii) material information,
    (iv) a recipe associated with the food item, and
    (v) medical information associated with the food item.

4. The electronic device of claim 1, wherein the feature comprises at least one of an image descriptor, MPEG standards Compact Descriptors for Visual Search (CDVS), Histograms of Oriented Gradient (HOG) feature, Scale Invariant Feature Transform (SIFT) feature, dense-SIFT feature, and Speeded Up Robust Features (SURF) feature.

5. The electronic device of claim 1, wherein:
    the at least one processor is further configured to select a portion of the first image that includes the object, and the feature is extracted from the portion.

6. The electronic device of claim 1, wherein the at least one processor is further configured to: obtain additional information associated with the first image; and transmit the additional information to the server, the at least one processor further configured to:
    when an image gallery is executed, control a display to display a list of selectable predetermined categories including the category into which the first image is classified, and
    in response to detecting selection of the category from the displayed list, control the display to display a notification indicating the analysis information is received from the server.

7. The electronic device of claim 6, wherein the additional information comprises metadata associated with the first image.

8. The electronic device of claim 6, wherein the additional information comprises an indication of a time when the first image is obtained and/or an indication of a location where the first image is obtained.

9. The electronic device of claim 1, wherein the at least one processor is further configured to transmit, to the server, user information associated with the electronic device.

10. The electronic device of claim 1, wherein the memory is configured to store a second image, and the at least one processor is further configured to:
    compare the first image to the second image; and
    extract the feature from the first image in response to detecting that the first image matches the second image.

11. The electronic device of claim 10, wherein:
    comparing the second image to the first image includes generating a score indicating a degree of similarity between the first image and the second image, and
    the at least one processor is further configured to detect whether the first image matches the second image based on the score.

12. The electronic device of claim 1, wherein the analysis information is provided through an application that is executed by the at least one processor.

13. The electronic device of claim 1, further comprising a display, wherein the processor is further configured to control the display to display the analysis information.

14. A server, comprising:
    a memory;
    a communication circuit; and
    at least one processor operatively coupled to the memory and the communication circuit, configured to:
        receive, from an electronic device, a feature of an object depicted in a first image classified according to a first comparison executed by the electronic device, through the communication circuit;
        analyze the feature by executing a second comparison to retrieve analysis information corresponding to the feature; and
        control the communication circuit to transmit the analysis information to the electronic device,
    wherein an indication of the feature comprises at least one of a MPEG standards Compact Descriptors for Visual Search (CDVS), Histograms of Oriented Gradient (HOG) feature, Scale Invariant Feature Transform (SIFT) feature, dense-SIFT feature, and Speeded Up Robust Features (SURF) feature.

15. The server of claim 14, wherein:
    the at least one processor is further configured to identify a second image that matches to the feature; and
    the analysis information is obtained based on the second image.

16. The server of claim 14, wherein:
    the at least one processor is further configured to receive, from the electronic device, additional information associated with the first image, and
    the analysis information is obtained based on a second image that matches to the feature and the additional information.

17. The server of claim 16, wherein the additional information comprises at least one of an indication of a time when the first image is obtained and an indication of a location where the first image is obtained.

18. The server of claim 14, wherein:
the memory is configured to store an analysis history database containing analysis information previously obtained by a plurality of users,
the at least one processor is further configured to receive user information associated with the electronic device, and
the analysis information is obtained based on the user information and previous analysis information that is retrieved from the analysis history database.

19. A method, comprising:
obtaining, by an electronic device, an image and classifying the image by executing a first comparison on the image;
in response to detecting that the image is classified into a category of images stored in a memory, extracting, by the electronic device, a feature on an object depicted in the image;
transmitting an indication of the feature to a server executing a second comparison on the feature to retrieve analysis information corresponding to the feature; and
receiving the analysis information associated with the object from the server.

20. The method of claim 19, wherein the feature comprises at least one of an image descriptor, MPEG standards Compact Descriptors for Visual Search (CDVS), Histograms of Oriented Gradient (HOG) feature, Scale Invariant Feature Transform (SIFT) feature, dense-SIFT feature, and Speeded Up Robust Features (SURF) feature, the method further comprising:
in response to detecting a selection of a food item category from among a plurality of categories, controlling a display to display a selectable option to add the object to a list together with at least a portion of the analysis information received from the server.

* * * * *